United States Patent [19]

Au

[11] Patent Number: 4,471,140

[45] Date of Patent: Sep. 11, 1984

[54] PREPARATION OF AROMATIC ALDEHYDES

[75] Inventor: Andrew T. Au, Needham, Mass.

[73] Assignee: The Dow Chemical Company, Midland, Mich.

[21] Appl. No.: 409,748

[22] Filed: Aug. 19, 1982

[51] Int. Cl.$^3$ ............................................. C07C 45/28
[52] U.S. Cl. ................................................ 568/432
[58] Field of Search ............................... 568/431, 432

[56] References Cited

FOREIGN PATENT DOCUMENTS 0012939  7/1980  European Pat. Off. .

OTHER PUBLICATIONS

Eley et al., Advances in Catalysis, vol. 25, (1976), 272–339, 390–413.

Primary Examiner—Bernard Helfin
Attorney, Agent, or Firm—Douglas N. Deline

[57] ABSTRACT

Aromatic aldehydes are formed by the liquid phase reaction of molecular oxygen with methyl-substituted aromatic compounds in the presence of base, a cobalt, manganese, chromium or nickel salt catalyst and an easily removable amine.

13 Claims, No Drawings

PREPARATION OF AROMATIC ALDEHYDES

BACKGROUND OF THE INVENTION

The present invention relates to an improved process for the oxidation of methyl-substituted aromatic compounds. More particularly, the present invention comprises an improved liquid phase catalyst system for the preparation of aromatic aldehydes, especially p-hydroxybenzaldehyde.

In U.S. Pat. No. 4,113,782, formylated phenoxy compounds are prepared by air oxidation of methylated phenoxy compounds such as p-methoxytoluene in the liquid phase in the presence of co-catalysts comprising lower fatty acids or anhydrides and at least one soluble salt of cobalt, manganese, chromium or nickel.

In EP No. 12,939 to Sumitomo Chemical Company Ltd., p-cresol is oxidized in the liquid phase by an oxygen-containing gas in the presence of base and a cobalt compound or metallic cobalt. Cobalt porphyrin complex was disclosed as a suitable catalyst at page 7, line 4. Amines were taught to be suitable solvents, however, later research has indicated that amines in general are not suitable solvents.

SUMMARY OF THE INVENTION

According to the present invention, the catalytic oxidation of methyl-substituted aromatic compounds under basic conditions in the liquid phase by the action of an oxygen-containing gas in the presence of soluble cobalt, manganese, chromium or nickel salts is improved and advanced over previously known liquid phase processes by additionally adding to the system an easily removable amine.

DETAILED DESCRIPTION OF THE INVENTION

Methyl-substituted aromatic compounds that are selectively oxidized according to the present invention are those previously known and taught in the art. Suitable compounds are those of the formula

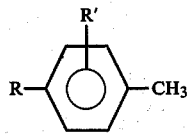

wherein R is hydroxyl or $C_{1-4}$ alkoxy, R' is halo, lower alkyl or hydrogen. Specific examples of suitable methyl-substituted aromatic compounds for use according to the invented process are p-cresol, 2,6-dichloro-p-cresol, 2-bromo-p-cresol, 2,4-xylenol, 3,4-xylenol, 2,6-di-tert-butyl-p-cresol, p-methoxytoluene, 4-methoxy-2,6-dichlorotoluene, etc.

Preferred methyl-substituted aromatic compounds are cresols, especially p-cresol, which is converted by the instant oxidation to p-hydroxybenzaldehyde. The aromatic aldehyde products of the instant process are known compounds having utility as intermediates in the preparation of pharmaceuticals, agricultural chemicals, polymeric resins and other industrial chemicals.

The process is conducted in the liquid phase. While the methyl-substituted aromatic compound may itself form the liquid phase, it is preferred to add a liquid solvent. Suitable liquids are organic compounds that are inert under the reaction conditions employed and capable of dissolving the methyl-substituted aromatic compound. Examples include alcohols, ethers, halogenated hydrocarbons, dimethylformamide, dimethylsulfoxide, etc. The solvents may be employed in combination or singly. Preferred solvents are alcohols such as methanol, ethanol, isopropanol, butanol, tertiary butanol, ethylene glycol, etc.

Bases suitably employed include alkali metal or alkaline earth metal hydroxides, alkoxides or amides. Preferred for their ready availability and low cost are sodium or potassium hydroxide. The amount of base employed is from about 1 to about 20 equivalents per equivalent of methyl-substituted aromatic compound, preferably from about 2 to about 4 equivalents.

The oxidizing agent is oxygen which may be used singly or mixed with other inert gases. Air is the preferred oxygen-containing gas. The amount or concentration of oxygen is not particularly limited and may be suitably determined by due consideration of safety and convenience. Pressures from 1 to about 100 atmospheres are suitable.

The reaction temperature is suitably from about 0° C. to about 300° C. and preferably from about 25° C. to about 100° C.

The metal salt catalysts employed are soluble salts having either organic or inorganic anions. Suitable are halide, organic acid, oxide, hydroxide or inorganic acid salts of cobalt, manganese, chromium or nickel. Initially the metal may be added in any available valence. Examples of the metal salt catalysts of the invention are fluoride, chloride, bromide, iodide, acetate, oxalate, stearate, naphthenate, nitrate, sulfate, carbonate, oxide or hydroxide salts of the above metals. Preferred catalysts are divalent or trivalent cobalt salts.

The amount of soluble metal salt employed is not critical. Suitably from about 0.001 to 1, and preferably from about 0.01 to 0.1 equivalents of metal salt per equivalent of methyl-substituted aromatic compound may be employed.

Additionally present according to the instant process is an easily removable amine. By the term "easily removable" is meant amines that may be removed from the resulting product by volatilization, e.g., low boiling easily distillable amines, or those that are removed by treatment with aqueous acid.

Suitable amines are primary, secondary or tertiary aliphatic, cycloaliphatic or aromatic amines, or diamines of up to about 12 carbons. Examples of suitable easily removable amines include ammonia (either supplied as free ammonia or an ammonium salt such as ammonium hydroxide), trimethylamine, trietylamine, dimethylamine, dicyclohexylamine, ethylenediamine, tetramethylethylenediamine, piperidine, pyridine, dimethylaminopyridine, etc. Preferred easily removable amines are dialkylamines, trialkylamines, tetraalkyl-substituted ethylenediamines and cycloaliphatic amines. Most preferred amines are piperidine, ammonia, trimethylamine and triethylamine.

Because such easily removable amines may be distilled from the product or otherwise removed by acid washing, they are easily separated from the reaction products and reused if desired. The prior art catalyst, cobalt porphyrin, is not easily removable by either acid washing or distillation and is therefore present as a contaminant of the desired aromatic aldehyde or lost as part of the reaction tars. Considering the initial expense of porphyrin chelants compared to the present easily removable amines, their subsequent loss is a considerable economic waste. Therefore, the present invention offers a greatly improved method for preparing aromatic aldehydes.

The amine is employed in minor amounts sufficient to form complexes with the metal salt. A preferred amount is about a stoichiometric amount or a slight excess thereover up to about a 10 percent excess of a stoichiometric amount based on the complex formed.

SPECIFIC EMBODIMENTS

Having described the invention, the following examples are provided as further illustrative and are not to be construed as limiting its scope.

EXAMPLE 1

A mixture of 21.0 g of p-cresol, 24.0 g of crushed sodium hydroxide and 1.0 g of cobalt dichloride hexahydrate in 125 ml of methanol containing 20 drops of piperidine is stirred rapidly between 60° C.–65° C. while oxygen is bubbled into the mixture. After 18 hours, gas chromatograph results indicate almost total absence of p-cresol. The mixture is then cooled, neutralized with dilute HCl, saturated with NaCl and extracted with ethyl acetate. The extract is washed with saturated sodium chloride solution, dried over magnesium sulfate and concentrated to a brown solid (22.4 g). When crystallized from a 50/50 volume mixture of chloroform/hexane, 14.7 g of the desired parahydroxybenzaldehyde is collected on a filter (62.7 percent yield). This material is in every way identical to an authentic sample.

EXAMPLE 2

The reaction conditions of Example 1 are substantially repeated employing the easily removable amines further identified in Table I. In the tests 3.0 g of p-cresol, 3.6 g of NaOH, 25 ml of methanol, 0.4 g of $CoCl_2.6H_2O$ and the indicated amine ae combined and stirred while $O_2$ is bubbled through the reaction mixture. Conversion is determined by gas chromatograph analysis after the indicated time period. Results are contained in Table I.

TABLE I

| Amine | Amount | % Conversion After 6 hours | 10 hours |
|---|---|---|---|
| None | — | 25 | 55 |
| (conc) NH$_4$OH | ~0.2 ml | 52 | 95 |
| tetramethylethylenediamine | ~0.2 ml | 66 | — |
| dicyclohexylamine | ~0.2 ml | 50 | — |
| 4-dimethylaminopyridine | 0.15 g | 50 | — |

What is claimed is:

1. A process for preparing aromatic aldehydes comprising contacting a methyl-substituted aromatic compound corresponding to the formula:

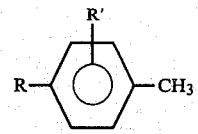

wherein R is hydroxyl or $C_{1-4}$ alkoxy, and R' is halo, lower alkyl or hydrogen, with an oxygen-containing gas at a pressure from about 1 to about 100 atmospheres and a temperature from about 0° C. to about 300° C. in the presence of base, a metal salt catalyst selected from the soluble organic or inorganic salts of cobalt, manganese, chromium and nickel, a liquid solvent and a minor amount sufficient to form a complex with the metal salt of an easily removable amine.

2. A process according to claim 1 wherein the easily removable amine is a primary, secondary or tertiary aliphatic, cycloaliphatic or aromatic amine or diamine of up to about 12 carbons.

3. A process according to claim 1 wherein the easily removable amine is selected from the group consisting of ammonia, trimethylamine, triethylamine, dimethylamine, tetramethylethylenediamine, piperidine and dimethylaminopyridine.

4. A process according to claim 1 wherein the metal salt catalyst is a metal hydroxide or a metal salt of an organic acid or inorganic acid.

5. A process according to claim 1 wherein the metal salt catalyst is a cobalt salt.

6. A process according to claim 1 wherein from about 0.001 to 1 equivalent of metal salt catalyst per equivalent of methyl-substituted aromatic compound is present.

7. A process according to claim 1 wherein a solvent is additionally present.

8. A process according to claim 7 wherein the solvent is an alcohol, ether, halogenated hydrocarbon, or mixture thereof.

9. A process according to claim 8 wherein the solvent is methanol.

10. A process according to claim 1 wherein the methyl-substituted aromatic compound is p-cresol and the aromatic aldehyde formed is p-hydroxybenzaldehyde.

11. A process according to claim 1 wherein the temperature is from about 25° C. to about 100° C.

12. A process according to claim 1 wherein the amount of easily removable amine is from about a stoichiometric amount based on the complex formed to about a 10 percent excess thereover.

13. A process according to claim 1 wherein the solvent is an alcohol.

* * * * *